US009782060B2

(12) United States Patent
Nemoto et al.

(10) Patent No.: US 9,782,060 B2
(45) Date of Patent: Oct. 10, 2017

(54) MEDICAL SYSTEM

(71) Applicant: OLYMPUS CORPORATION, Hachioji-shi, Tokyo (JP)

(72) Inventors: Iori Nemoto, Tokyo (JP); Kiyoshi Sekiguchi, Hachioji (JP); Yorito Maeda, Kiyose (JP); Takayuki Katsuyama, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/584,948

(22) Filed: May 2, 2017

(65) Prior Publication Data
US 2017/0231478 A1     Aug. 17, 2017

Related U.S. Application Data

(63) Continuation of application No. PCT/JP2016/059504, filed on Mar. 24, 2016.

(30) Foreign Application Priority Data

May 22, 2015  (JP) ................................. 2015-104790

(51) Int. Cl.
*G06F 3/041*     (2006.01)
*A61B 1/045*    (2006.01)
(Continued)

(52) U.S. Cl.
CPC .............. *A61B 1/045* (2013.01); *G06F 3/041* (2013.01); *G06F 3/1423* (2013.01);
(Continued)

(58) Field of Classification Search
USPC .................. 345/1.1, 1.3, 170–176; 725/41
See application file for complete search history.

(56) References Cited

U.S. PATENT DOCUMENTS 6,333,750 B1 * 12/2001 Odryna ..................... G06F 3/14
                                                                345/1.1
8,766,993 B1 *  7/2014 Hobbs ....................... G06F 3/14
                                                                345/536
(Continued)

FOREIGN PATENT DOCUMENTS

EP       2755385 A1     7/2014
JP    H08-126606 A      5/1996
(Continued)

OTHER PUBLICATIONS

Jun. 21, 2016 Search Report issued in International Application No. PCT/JP2016/059504.

*Primary Examiner* — Tony Davis
(74) *Attorney, Agent, or Firm* — Oliff PLC

(57) ABSTRACT

A medical system includes: a plurality of monitors each configured to display a video signal of a different type; a touch panel configured to display an operation screen where a selecting operation is performed; a video output discrimination portion configured to discriminate a monitor capable of displaying the video signal of the peripheral device for which the selecting operation is performed by referring to a table in which the peripheral device is associated with the monitor capable of displaying the video signal; a data holding portion configured to hold a monitor identification video for identifying the monitor capable of displaying the video signal and information on the corresponding monitor; and a peripheral device control portion configured to perform control so as to display the monitor identification video held in the data holding portion on the discriminated monitor, depending on a discrimination result of the video output discrimination portion.

4 Claims, 13 Drawing Sheets

(51) Int. Cl.
*H04N 7/18* (2006.01)
*G06T 7/00* (2017.01)
*G06F 3/14* (2006.01)
*G06F 3/147* (2006.01)
*G06F 3/153* (2006.01)

(52) U.S. Cl.
CPC ........... *G06T 7/0012* (2013.01); *H04N 7/181* (2013.01); *G06F 3/147* (2013.01); *G06F 3/153* (2013.01)

(56) References Cited

U.S. PATENT DOCUMENTS

| | | | | |
|---|---|---|---|---|
| 9,412,329 B2* | 8/2016 | Fullerton | ............... | G06F 3/1423 |
| 2001/0008535 A1* | 7/2001 | Lanigan | ............... | H04N 21/4341 |
| | | | | 370/487 |
| 2003/0210209 A1* | 11/2003 | Lagarrigue | ........... | H04N 7/0806 |
| | | | | 345/1.3 |
| 2004/0230094 A1* | 11/2004 | Nakamura | ........... | A61B 1/0005 |
| | | | | 600/101 |
| 2007/0024705 A1* | 2/2007 | Richter | .............. | H04N 7/17318 |
| | | | | 348/142 |
| 2007/0050828 A1* | 3/2007 | Renzi | .................... | H04N 7/141 |
| | | | | 725/93 |
| 2009/0054735 A1* | 2/2009 | Higgins | ............... | A61B 5/0006 |
| | | | | 600/300 |
| 2012/0194442 A1* | 8/2012 | Sheeley | ................ | G06F 3/0416 |
| | | | | 345/173 |
| 2013/0246576 A1* | 9/2013 | Wogsberg | .............. | H04N 7/181 |
| | | | | 709/219 |
| 2013/0265402 A1 | 10/2013 | Tashiro et al. | | |
| 2014/0101700 A1* | 4/2014 | Sheeley | ................ | H04N 5/222 |
| | | | | 725/41 |
| 2017/0105053 A1* | 4/2017 | Todd | ..................... | H04N 21/816 |

FOREIGN PATENT DOCUMENTS

| | | |
|---|---|---|
| JP | 2013-094593 A | 5/2013 |
| JP | 5351360 B2 | 11/2013 |
| JP | 2014-045239 A | 3/2014 |
| JP | 2016-036592 A | 3/2016 |
| WO | 2013/035384 A1 | 3/2013 |

* cited by examiner

FIG. 4

| IN No. | DEVICE | OUT No. |
|---|---|---|
| 1 | ROOM CAMERA | 1, 2 |
| 2 | OPERATING FIELD CAMERA | 1, 2 |
| 3 | 3D PROCESSOR | 3, 4 |
| 4 | 4K PROCESSOR | 5, 6 |
| 5 | — | — |
| 6 | SYSTEM CONTROLLER | — |

| DEVICE | MONITOR IDENTIFICATION VIDEO |
|---|---|
| ROOM CAMERA | ROOM CAMERA — 176 |
| OPERATING FIELD CAMERA | OPERATING FIELD CAMERA — 177 |
| 3D PROCESSOR | 3D PROCESSOR — 178 |
| 4K PROCESSOR | 4K PROCESSOR — 179 |

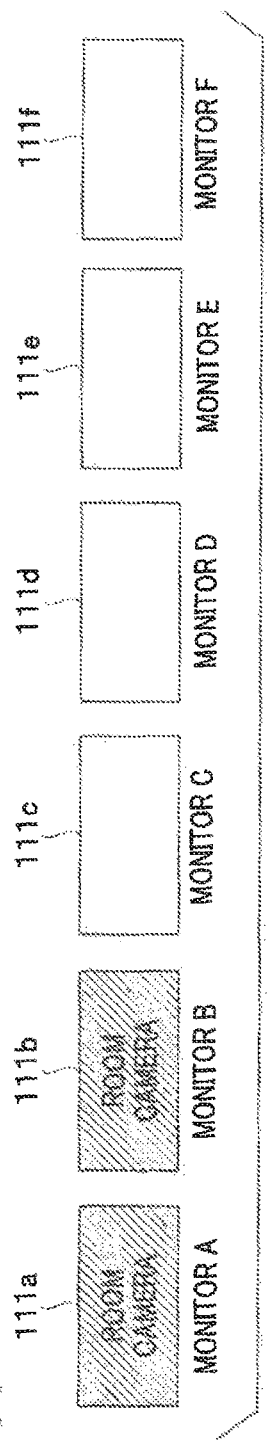
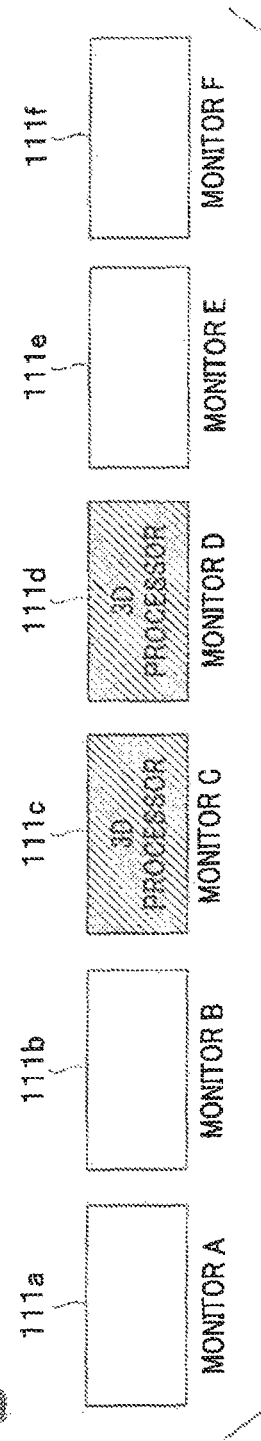
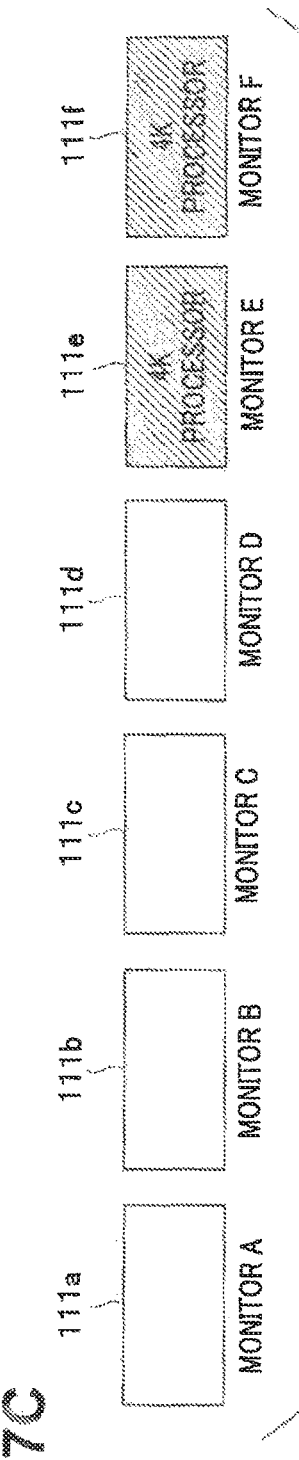

FIG. 9

| OUT No. | MONITOR TYPE |
|---|---|
| 1 | 2D |
| 2 | 2D |
| 3 | 3D |
| 4 | 3D |
| 5 | 4K |
| 6 | 4K |

| MONITOR TYPE | MONITOR IDENTIFICATION VIDEO OUTPUT DESTINATION (OUT No.) |
|---|---|
| 2D | 1, 2 |
| 3D | 3, 4 |
| 4K | 5, 6 |

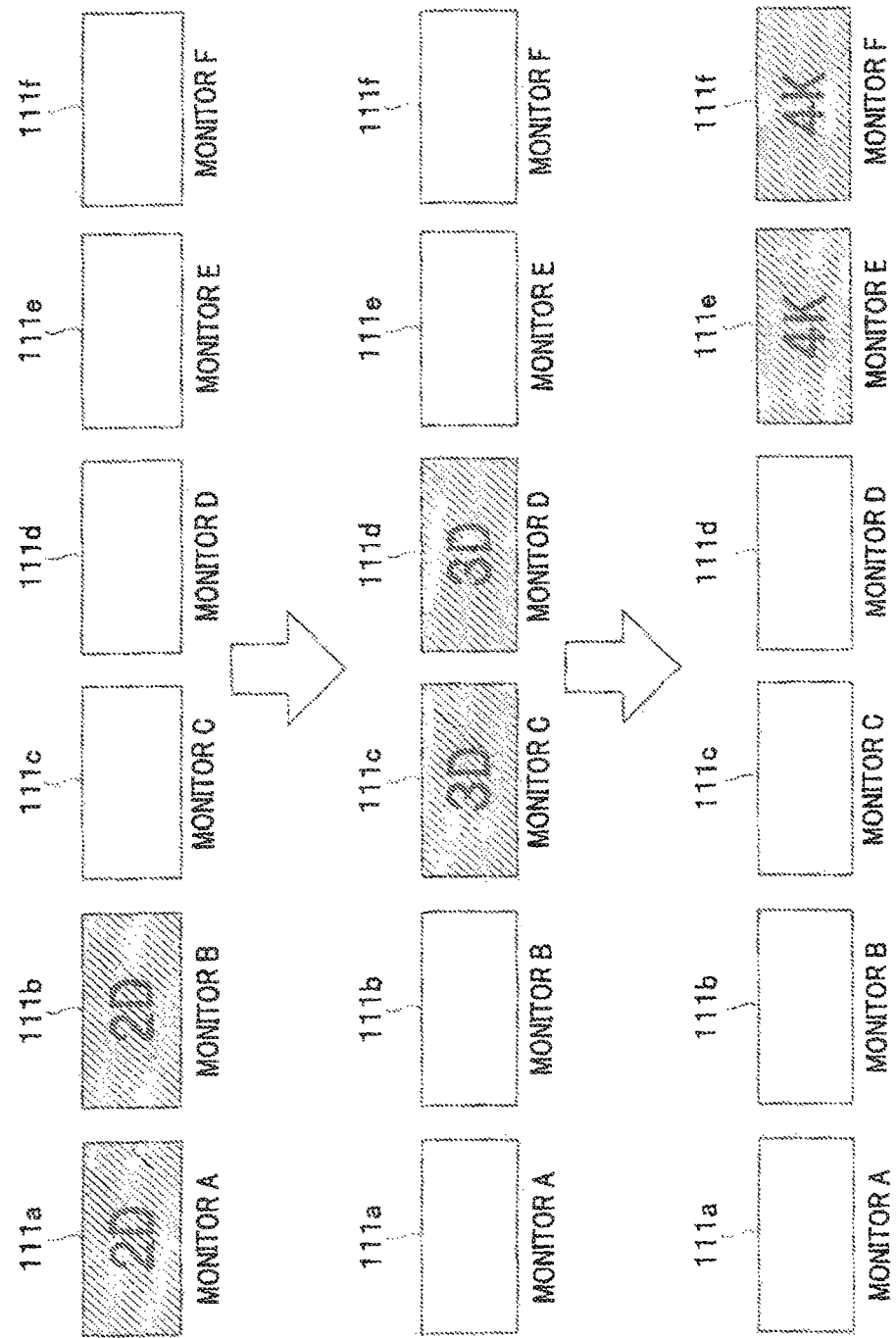

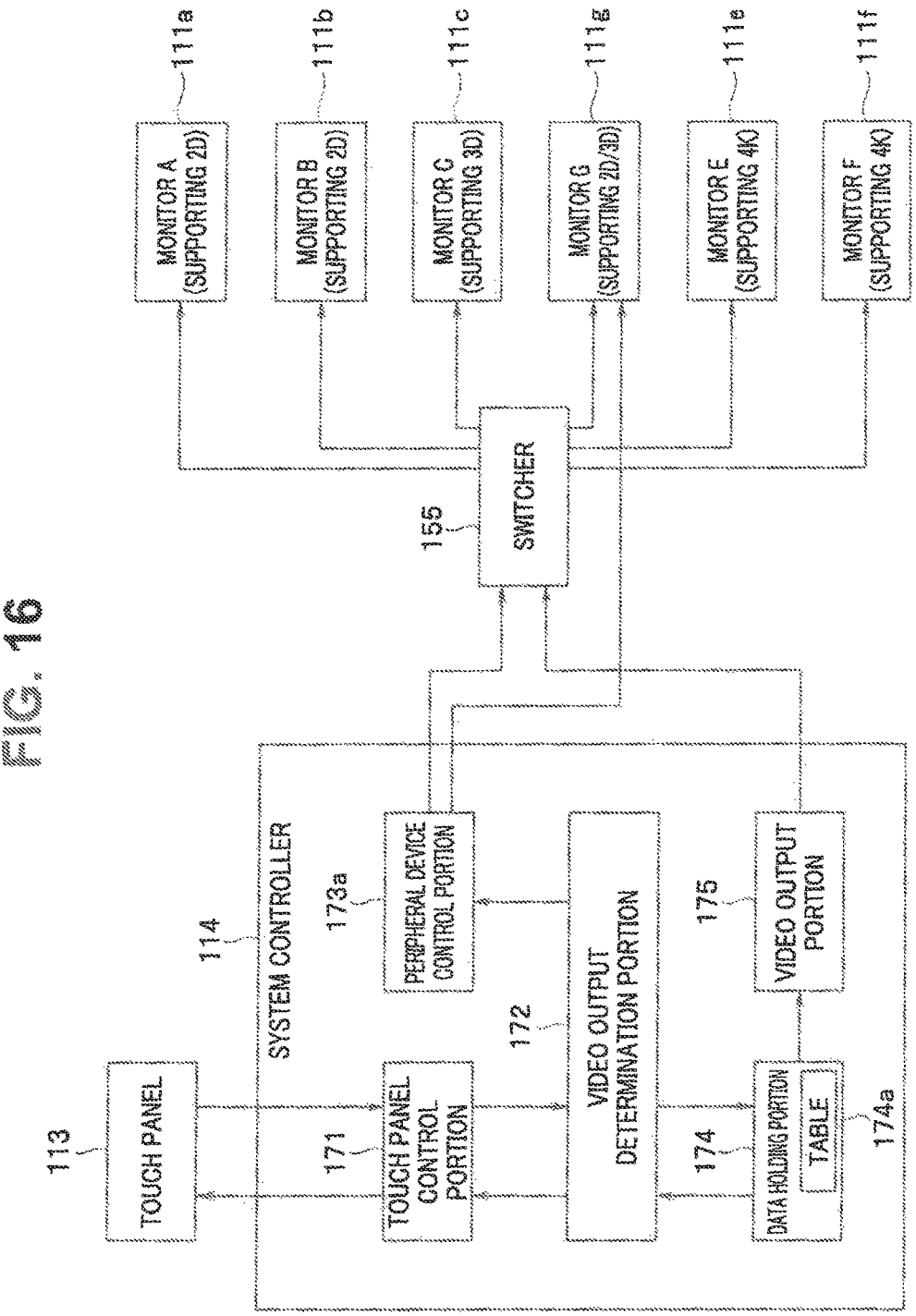

MEDICAL SYSTEM

CROSS REFERENCE TO RELATED APPLICATION

This application is a continuation application of PCT/JP2016/059504 filed on Mar. 24, 2016 and claims benefit of Japanese Application No. 2015-104790 filed in Japan on May 22, 2015, the entire contents of which are incorporated herein by this reference.

BACKGROUND OF THE INVENTION

1. Field of the Invention

The present invention relates a medical system including a plurality of monitors each configured to display a video signal of a different kind.

2. Description of the Related Art

In recent years, medical devices have been becoming rich in variety, and functions of the medical devices also have been becoming enriched together with development of technologies. In an operating room, procedures need to be carried out with reference to various kinds of medical information obtained from the devices such as X-ray fluoroscopic images, endoscope images and a heart rate, so that, generally, a plurality of monitors are arranged inside the room and respective pieces of the information are displayed on respective screens.

For example, Japanese Patent Application Laid-Open Publication No. 2013-94593 discloses an endoscope system including a plurality of monitors in an operating room and configured to determine a transmission destination of a medical image to be a monitor not displaying a video based on display states of the plurality of monitors.

Conventionally, since an endoscope image obtained from an endoscope apparatus is a two-dimensional image, a monitor supporting two dimensions is sufficient as a monitor to display the endoscope image. However, in recent years, an endoscope apparatus capable of acquiring a three-dimensional endoscope image or a 4K endoscope image has been put in practical use, and a monitor supporting three dimensions or supporting 4K has been used as a monitor to display medical information.

SUMMARY OF THE INVENTION

A medical system of one aspect of the present invention includes: a plurality of monitors each configured to display a video signal of a different type; a touch panel configured to display an operation screen where a selecting operation of an output destination of a video signal of a peripheral device is performed; a video signal discrimination portion configured to discriminate, among the plurality of monitors, a monitor capable of displaying the video signal of the peripheral device for which the selecting operation is performed by the touch panel by referring to a table in which the peripheral device is associated with the monitor capable of displaying the video signal; a monitor information holding portion configured to hold a monitor identification video for identifying the monitor capable of displaying the video signal and information on the corresponding monitor; and a control portion configured to perform control so as to display the monitor identification video held in the monitor information holding portion on the discriminated monitor, depending on a discrimination result of the video signal discrimination portion.

BRIEF DESCRIPTION OF THE DRAWINGS

FIG. 4 is a diagram for describing one example of a setting table 174a;

FIG. 5 is a diagram for describing one example of a device connected to an input terminal and a monitor identification video corresponding to the device;

FIG. 7A is a diagram for describing one example of a video outputted to a monitor;

FIG. 7B is a diagram for describing one example of the video outputted to the monitor;

FIG. 7C is a diagram for describing one example of the video outputted to the monitor;

FIG. 9 is a diagram for describing one example of a monitor type set by a user;

FIG. 10 is a diagram for describing one example of a setting table 174b;

FIG. 15 is a diagram for describing one example of the video outputted to the monitor, and FIG. 16 is a diagram describing one example of the detailed circuit configuration of the system controller 114.

DETAILED DESCRIPTION OF THE PREFERRED EMBODIMENTS

Hereinafter, embodiments will be described with reference to the drawings.

First Embodiment

Figure 1:
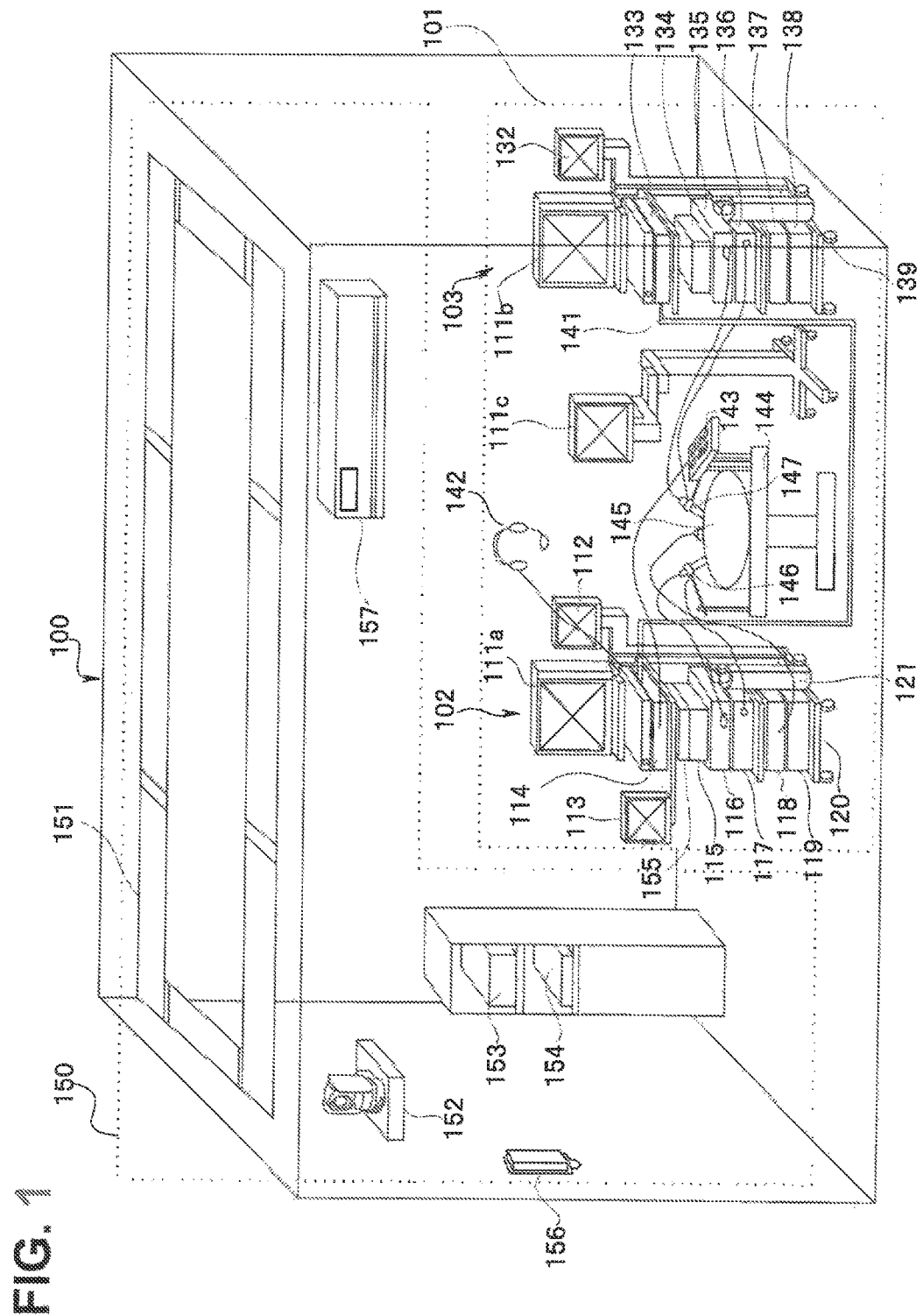
FIG. 1 is a diagram describing one example of an entire configuration of a medical system 100 relating to a first embodiment of the present invention.

FIG. 1 is a diagram describing one example of an entire configuration of a medical system 100 relating to the first embodiment of the present invention. As illustrated in FIG. 1, the medical system 100 of the present embodiment is comprises a medical device control system 101 and a non-medical device control system 150. The medical device control system 101 is a system formed of a plurality of medical devices and a system controller 114 configured to control the medical devices. The non-medical device control system 150 is a system formed of non-medical devices related to a surgery and a system controller 153 configured to control the non-medical devices.

First, the medical device control system 101 will be described with a case of an endoscopic surgery as one example. In an operating room, on both sides of a bed 144 where a patient 145 lies down, a first endoscopic surgery system 102, a second endoscopic surgery system 103, and a wireless remote controller 143 for an operator are arranged. For the first endoscopic surgery system 102, a plurality of endoscope peripheral devices configured to perform observation, inspections, treatment and recording or the like are loaded on a first trolley 120. For the second endoscopic surgery system 103, similarly, a plurality of endoscope peripheral devices configured to perform the observation, the inspections, the treatment and the recording or the like are loaded on a second trolley 139.

In the first trolley 120, a medical image display panel 111a, a central display panel 112, a central operation panel device 113, the system controller 114, a recorder 115, a video processor 116, an endoscope light source device 117, a pneumoperitoneum device 118, an electrocautery device 119, and a switcher 155 are arranged.

The medical image display panel 111a is a display device such as a liquid crystal display, and a video signal inputted from the video processor 116 through the system controller 114 and the switcher 155, that is, an endoscopic image of a lesion or the like is displayed. Note that, on the medical image display panel 111a, other than the endoscopic image, an operating field image photographed by an operating field camera not shown in the figure or the like can be also displayed. By operating the switcher 155, an image to be displayed on the medical image display panel 111a can be selected.

The central display panel 112 is display means capable of selectively displaying any data during a surgery. The central operation panel device 113 is configured by a display portion such as a liquid crystal display and a touch sensor for example integrally provided on the display portion, and is a central operation device configured to allow a nurse or the like in a non-sterilized area to intensively manage, control and operate the respective medical devices. Operation information instructed by the central operation panel device 113 is inputted to the system controller 114, and used for controlling the respective medical devices connected to the system controller 114.

Note that, to the system controller 114, the medical image display panel 111a, the central display panel 112, the central operation panel device 113, the recorder 115, the video processor 116, the endoscope light source device 117, the pneumoperitoneum device 118, and the electrocautery device 119 are connected through a communication cable such as a serial interface cable not shown in the figure. Therefore, using the central operation panel device 113, the medical devices can be controlled.

In addition, to the system controller 114, a headset type microphone 142 can be connected. Not only the respective devices connected to the system controller 114 are controlled from the central operation panel device 113 by the nurse or the like in the non-sterilized area but also voice inputted from the headset type microphone 142 is recognized and the respective devices can be controlled by the voice of an operator in a sterilized area.

The endoscope light source device 117 is connected to a first endoscope 146 through a light guide cable configured to transmit illumination light radiated from a lamp. The illumination light from the endoscope light source device 117 irradiates the lesion or the like inside an abdominal region of the patient 145 into which an insertion portion of the first endoscope 146 is inserted, when supplied to the first endoscope 146.

On a proximal end side of the insertion portion of the first endoscope 146, a camera head including an image pickup device is mounted, and an optical image of the lesion or the like is picked up by the image pickup device inside the camera head. An image pickup signal picked up by the image pickup device is transmitted to the video processor 116 through a camera cable. The video processor 116 executes predetermined signal processing on the transmitted image pickup signal, and generates the video signal. Then, the video processor 116 outputs the generated video signal to the system controller 114. The system controller 114 outputs the video signal to a selected medical image display panel 111 among the medical image display panels 111 connected to the switcher 155 through the switcher 155, and causes the video signal to be displayed.

A carbon dioxide gas cylinder 121 is connected to the pneumoperitoneum device 118, and carbon dioxide gas is supplied into the abdominal region of the patient 145 through a trocar. The electrocautery device 119 is connected with an active electrode and a patient plate installed under a body of the patient 145, and cauterizes a body surface and the lesion or the like.

In the second trolley 139, a medical image display panel 111b, a central display panel 132, a relay unit 133, a recorder 134, a video processor 135, an endoscope light source device 136, and other medical devices 137 and 138 (for example, an ultrasound processor, a lithotripter, a pump, or a shaver) are loaded. The respective devices are connected to the relay unit 133 by a cable not shown in the figure, and bidirectional communication is made possible. In addition, the system controller 114 and the relay unit 133 are connected by a relay cable 141.

Similarly to the medical image display panel 111a, the medical image display panel 111b is a display device such as a liquid crystal display, and the video signal inputted from the video processor 135 through the system controller 114 and the switcher 155, that is, the endoscopic image of the lesion or the like is displayed. Note that, on the medical image display panel 111b, other than the endoscopic image, the operating field image photographed by the operating field camera not shown in the figure or the like can be also displayed. By operating the switcher 155, the image to be displayed on the medical image display panel 111b can be selected.

The endoscope light source device 136 is connected to a second endoscope 147 through a light guide cable configured to transmit the illumination light radiated from the lamp. The illumination light from the endoscope light source device 136 irradiates the lesion or the like inside the abdominal region of the patient 145 into which the insertion portion of the second endoscope 147 is inserted, when supplied to the second endoscope 147.

On the proximal end side of the insertion portion of the second endoscope 147, a camera head including an image pickup device is mounted, and the optical image of the lesion or the like is picked up by the image pickup device inside the camera head. The image pickup signal picked up by the image pickup device is transmitted to the video processor 135 through the camera cable. The video processor 135 executes the predetermined signal processing on the transmitted image pickup signal, and generates the video signal. The generated video signal is outputted to the medical image display panel 111b or the like through the system controller 114 and the switcher 155, and displayed as the endoscopic image of the lesion or the like.

Note that, on the first trolley 120 and the second trolley 139, devices other than the devices described above (for example, a printer and an ultrasound observation device) can be also loaded. In addition, on a movable stand, a medical image display panel 111c is loaded.

The switcher 155 as an input/output switching portion includes a plurality of input terminals and output terminals, and is capable of outputting an image signal inputted from a desired input terminal to the display device connected to a desired output terminal and causing the image signal to be displayed. For example, in the case that the video processors 116 and 135 are connected to each of two input terminals and the medical image display panels 111a, 111b and 111c are connected to each of three output terminals, the endoscopic image picked up by the first endoscope 146 inputted from the video processor 116 can be displayed on the medical image display panel 111a, and can be also displayed on the medical image display panel 111b or the medical image display panel 11I c. A combination of the input terminal and the output terminal can be set using the central operation panel device 113.

Next, the non-medical device control system 150 will be described with non-medical devices used in the endoscopic surgery as one example. In the operating room, the non-medical devices such as a room light 151 for lighting the room, a room camera 152 for photographing the video of the entire room, a DVD player 154 for playing back recorded surgery video, a telephone 156 for communicating with outside of the operating room, and an air conditioner 157 for controlling an air condition of the room are arranged. The non-medical devices are connected with the system controller 153, and can be intensively controlled by the system controller 153.

Note that, while the medical system 100 provided in the operating room where the endoscopic surgery is performed is illustrated in FIG. 1, an application of the medical system 100 is not limited to the endoscopic surgery and the medical system 100 may be used for other surgeries or medical examinations. In addition, the medical system 100 may be provided somewhere other than the operating room, such as an examination room. The medical system 100 may include various devices and equipment not shown in FIG. 1, further.

Figure 2:
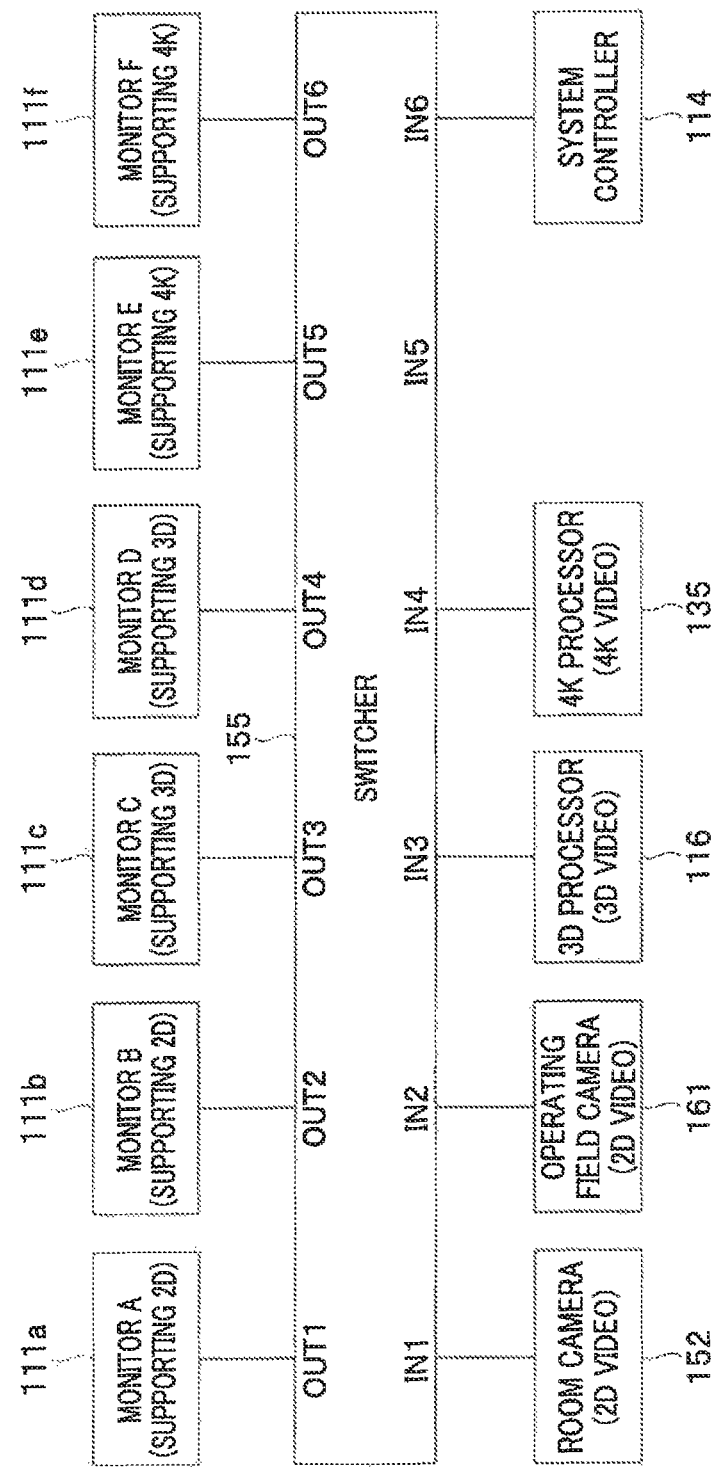
FIG. 2 is a diagram describing one example of a configuration of a switcher 155 and devices connected to the switcher 155.

Next, the configuration of the switcher 155 and the device connected to the switcher 155 will be described using FIG. 2. FIG. 2 is a diagram describing one example of the configuration of the switcher 155 and the devices connected to the switcher 155.

As illustrated in FIG. 2, to the switcher 155, the room camera 152 configured to photograph the video of the entire room and output a two-dimensional video signal, an operating field camera 161 configured to photograph the operating field and output the two-dimensional video signal, a 3D processor 116 configured to process the image pickup signal picked up by the first endoscope 146 and generate and output a three-dimensional video signal, a 4K processor 135 configured to process the image pickup signal picked up by the second endoscope 147 and generate and output a 4K video signal, and the system controller 114 are connected.

The room camera 152 is connected to an input terminal IN1, and the operating field camera 161 is connected to an input terminal IN2. In addition, the 3D processor 116 is connected to an input terminal IN3, the 4K processor 135 is connected to an input terminal IN4, and the system controller 114 is connected to an input terminal IN6. Then, no device is connected to an input terminal IN5.

On the other hand, to the output terminals of the switcher 155, the plurality of medical image display panels (indicated as a monitor A to a monitor F, hereinafter) 111a-111f are connected. A monitor A111a and a monitor B111b are 2D-supporting monitors capable of displaying a two-dimensional image. In addition, a monitor C111c and a monitor D111d are 3D-supporting monitors capable of displaying a three-dimensional image. Further, a monitor E111e and a monitor F111f are 4K-supporting monitors capable of displaying a 4K image. In this way, the plurality of monitors A111a-F111f display the video signal of a different type.

The monitor A111a is connected to an output terminal OUT1, and the monitor B111b is connected to an output terminal OUT2. In addition, the monitor C111c is connected to an output terminal OUT3, and the monitor D111d is connected to an output terminal OUT4. Further, the monitor E111e is connected to an output terminal OUT5, and the monitor F111f is connected to an output terminal OUT6. Furthermore, the monitors A111a-F111f are connected also with an input terminal not shown in the figure of the switcher 155 such that a return video signal is inputted to the switcher 155.

Figure 3:
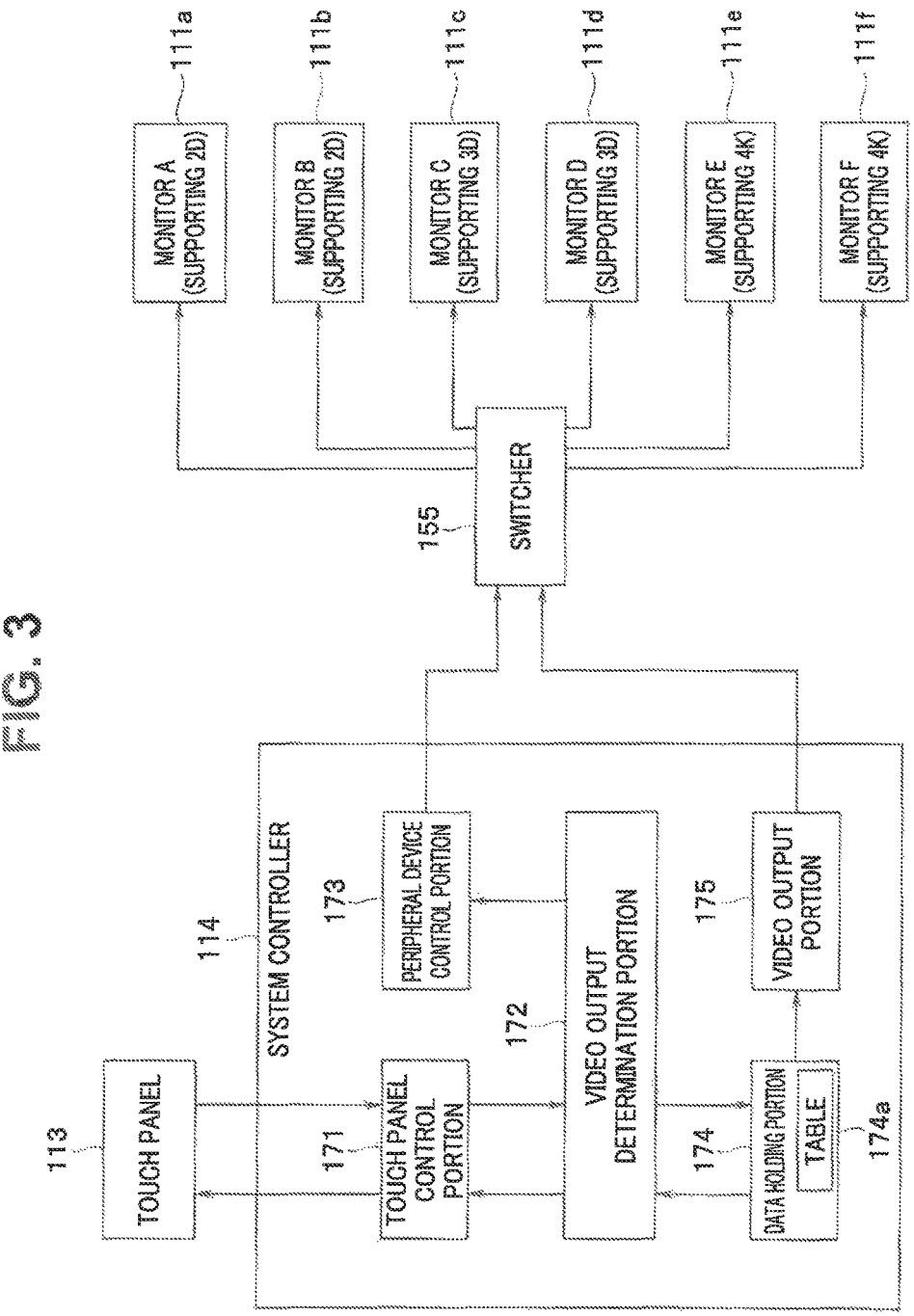
FIG. 3 is a diagram describing one example of a detailed circuit configuration of a system controller 114.

Next, a detailed circuit configuration of the system controller 114 will be described using FIG. 3. FIG. 3 is a diagram describing one example of the detailed circuit configuration of the system controller 114.

As illustrated in FIG. 3, to the system controller 114, the central operation panel device (indicated as a touch panel, hereinafter) 113 is connected. In addition, the system controller 114 is configured including a touch panel control portion 171, a video output determination portion 172, a peripheral device control portion 173, a data holding portion 174, and a video output portion 175. The data holding portion 174 includes a setting table 174a of the switcher. Note that the setting table 174a is configured to be included in the data holding portion 174, however, without being limited to the configuration, the setting table 174a may be configured to be included in the video output determination portion 172, for example.

FIG. 4 is a diagram for describing one example of the setting table 174a. As illustrated in FIG. 4, in the setting table 174a, the device connected to the input terminal is associated with the monitor to which the device can output the video. More specifically, in the setting table 174a, the device connected to the input terminal is associated with the output terminal connected to the monitor to which the device can output the video.

For example, as illustrated in FIG. 2, the room camera 152 configured to output a 2D video is connected to the input terminal IN1 of the switcher 155. Then, the monitors capable of displaying the 2D video are the monitor A111a connected to the output terminal OUT1 of the switcher 155 and the monitor B111b connected to the output terminal OUT2. Therefore, the output terminals OUT1 and OUT2 are set as output destinations of the room camera 152.

Since the device connected to the switcher 155 is different for each surgery, a user presets the setting table 174a by operating the touch panel 113 according to a connection situation of the switcher 155. That is, the user sets the device connected to the input terminal and the output destination of the video from the device beforehand by operating the touch panel 113. The setting table 174a set in this way is held in the data holding portion 174. Note that a name of the device in the setting table 174a can be edited using the touch panel 113.

In addition, in the data holding portion 174 as a monitor information holding portion, the device connected to the input terminal and a monitor identification video are held in correspondence, and also information on a peripheral device operation screen to be displayed on the touch panel 113 is held.

Figure 6:
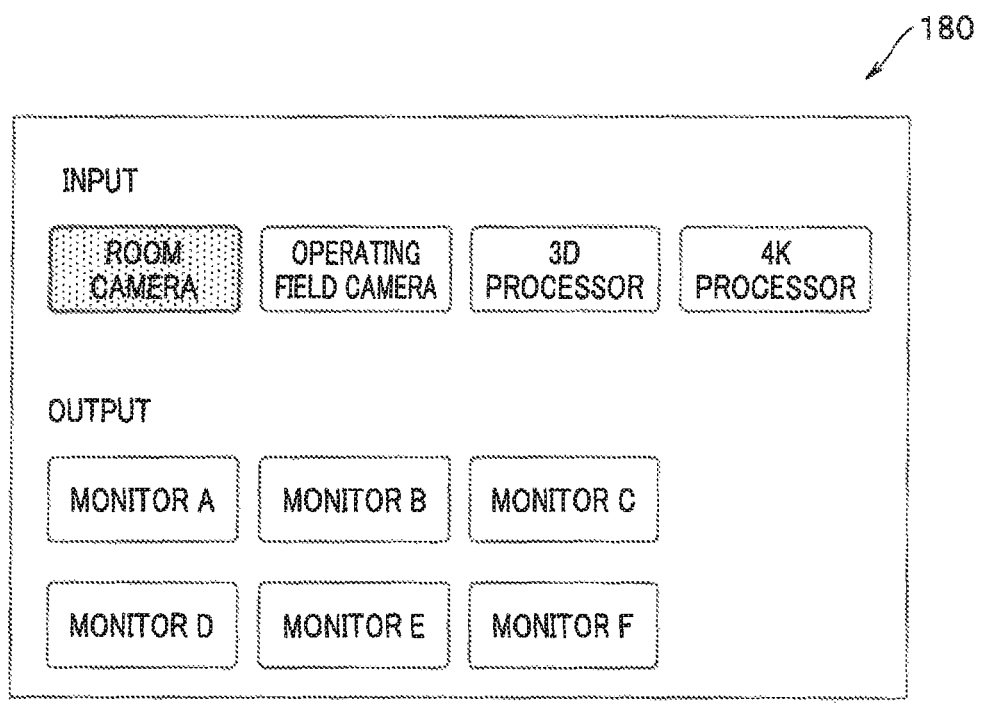
FIG. 6 is a diagram for describing one example of a peripheral device operation screen.

FIG. 5 is a diagram for describing one example of the device connected to the input terminal and the monitor identification video corresponding to the device, and FIG. 6 is a diagram for describing one example of the peripheral device operation screen.

As illustrated in FIG. 5, a monitor identification video 176 indicating the room camera by outline characters is associated with the room camera 152. Similarly, a monitor identification video 177 indicating the operating field camera by outline characters is associated with the operating field camera 161, a monitor identification video 178 indicating the 3D processor by outline characters is associated with the 3D processor 116, and a monitor identification video 179 indicating the 4K processor by outline characters is associated with the 4K processor 135. Note that the monitor identification videos 176-179 can be edited using the touch panel 113.

In addition, as illustrated in FIG. 6, in the data holding portion 174, the information on a peripheral device operation screen 180 for operating the peripheral device is held. On the peripheral device operation screen 180, input buttons indicating the devices connected to the input terminals of the switcher 155 and the devices connected to the output terminals of the switcher 155 are displayed. Note that display of the respective input buttons on the peripheral device operation screen 180 can be edited using the touch panel 113. Furthermore, the input button of the device not connected to the switcher 155 may be displayed in a gray color for example and made non-depressible, or may not be displayed.

The information on the peripheral device operation screen 180 is read from the data holding portion 174 by the video output determination portion 172, and outputted to the touch panel control portion 171. The touch panel control portion 171 performs control of outputting the video of the peripheral device operation screen 180 to the touch panel 113. Thus, the peripheral device operation screen 180 is displayed on the touch panel 113.

When the user depresses the room camera, as illustrated in FIG. 6, for example, on the peripheral device operation screen 180 displayed on the touch panel 113, a touch panel depression signal is outputted to the touch panel control portion 171. The touch panel control portion 171 outputs the touch panel depression signal to the video output determination portion 172.

The video output determination portion 172 as a video signal discrimination portion discriminates where on the touch panel 113 is depressed from the touch panel depression signal. In this example, it is discriminated that the room camera is depressed. When it is discriminated that the room camera is depressed on the peripheral device operation screen 180, the video output determination portion 172 outputs a video selection signal indicating the room camera to the data holding portion 174. In the data holding portion 174, the monitor identification video 176 corresponding to the room camera is outputted to the video output portion 175 according to the video selection signal. The video output portion 175 outputs the monitor identification video 176 from the data holding portion 174 to the switcher 155.

In addition, when it is recognized that the room camera is depressed on the peripheral device operation screen 180, the video output determination portion 172 refers to the setting table 174a, and acquires switcher setting information. In the case of this example, the video output determination portion 172 acquires the switcher setting information that the output destinations of the video are the output terminals OUT1 and OUT2 from the setting table 174a. The video output determination portion 172 outputs the switcher setting information to the peripheral device control portion 173.

The peripheral device control portion 173 as a control portion outputs a switcher control signal to the switcher 155, based on the switcher setting information from the video output determination portion 172. In the case of this example, the switcher control signal is a control signal to output the video from the system controller 114 connected to the input terminal IN6 to the monitor A111a connected to the output terminal OUT1 and the monitor B111b connected to the output terminal OUT2.

The switcher 155 outputs the monitor identification video 176 from the video output portion 175 to the monitor A111a and the monitor B111b, according to the switcher control signal from the peripheral device control portion 173.

FIG. 7A, FIG. 7B, and FIG. 7C are diagrams for describing one example of the video outputted to the monitor. As described above, in the case that the room camera is depressed on the peripheral device operation screen 180, as illustrated in FIG. 7A, the monitor identification video 176 in FIG. 5 is displayed on the monitor A111a and the monitor B111b. Similarly, in the case that the operating field camera is depressed on the peripheral device operation screen 180, the monitor identification video 177 in FIG. 5 is displayed on the monitor A111a and the monitor B111b.

In addition, in the case that the 3D processor is depressed on the peripheral device operation screen 180, as illustrated in FIG. 7B, the monitor identification video 178 in FIG. 5 is displayed on the monitor C111c and the monitor D111d. Similarly, in the case that the 4K processor is depressed on the peripheral device operation screen 180, as illustrated in FIG. 7C, the monitor identification video 179 in FIG. 5 is displayed on the monitor E111e and the monitor F111f.

Figure 8:
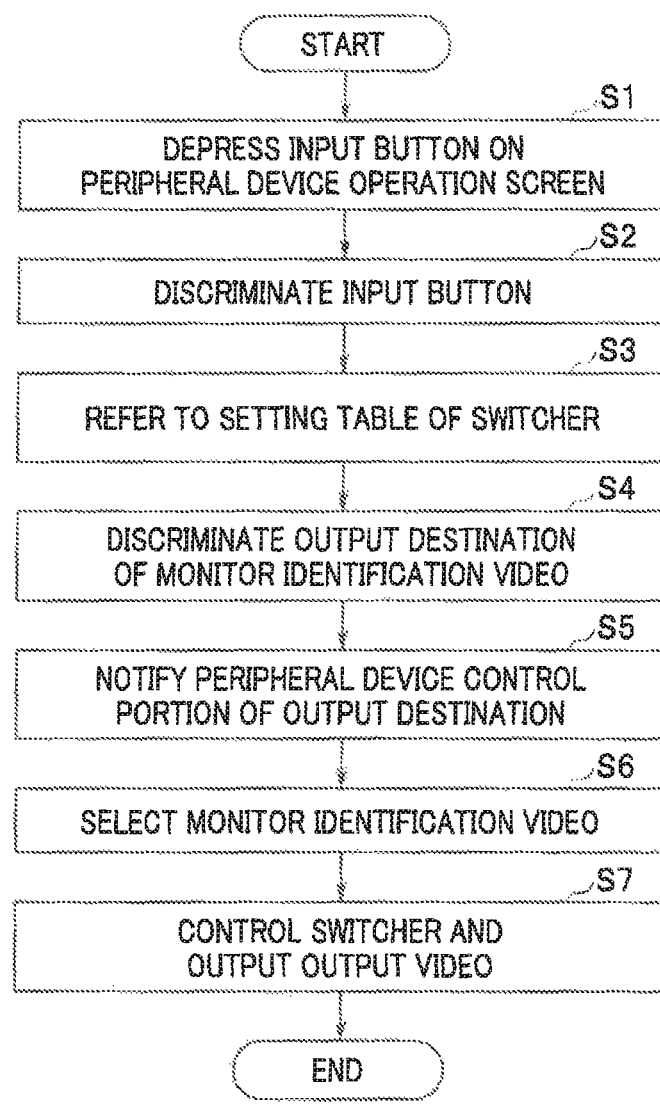
FIG. 8 is a flowchart for describing one example of a flow of output processing of the monitor identification video.

Next, output processing of the monitor identification video in the medical system 100 configured in this way will be described. FIG. 8 is a flowchart for describing one example of a flow of the output processing of the monitor identification video.

First, the input button on the peripheral device operation screen 180 is depressed by the user (step S1). The touch panel depression signal at the time is inputted through the touch panel control portion 171 to the video output determination portion 172. Next, the video output determination portion 172 discriminates the depressed input button from the touch panel depression signal (step S2). Then, the video output determination portion 172 refers to the setting table 174a of the switcher preset in the data holding portion 174 (step S3), and discriminates the output destination of the monitor identification video (step S4). The video output determination portion 172 notifies the peripheral device control portion 173 of the output destination discriminated in step S4 (step S5).

Next, the video output determination portion 172 selects the monitor identification video corresponding to the input button discriminated in step S2, and instructs the data holding portion 174 to output the monitor identification video to the video output portion 175 (step S6). Finally, the peripheral device control portion 173 controls the switcher 155 according to a notice in step S5, and outputs the monitor identification video from the video output portion 175 to the monitor A111a to the monitor F111f capable of displaying the monitor identification video from the video output portion 175 (step S7), and the processing is ended.

As described above, the system controller 114 controls the switcher 155 and outputs the monitor identification videos 176-179 held by the data holding portion 174 to the monitors A111a-F111f capable of displaying the monitor identification video. Since displayable device names are displayed on the respective monitors A111a-F111f, the user can easily identify the monitors A111a-F111f to which the device can output the video.

Therefore, according to the medical system of the present embodiment, the device capable of outputting the video signal to the monitor connected to the switcher can be easily recognized.

Second Embodiment

Next, the second embodiment will be described. Note that the entire configuration of the medical system 100 in the second embodiment and the configuration of the devices connected to the switcher 155 are respectively similar to FIG. 1 and FIG. 2 of the first embodiment, and only the configuration different from the first embodiment will be described below.

FIG. 9 is a diagram for describing one example of a monitor type set by the user. As illustrated in FIG. 9, the user sets a type of the monitors A111a-F111f connected to the output terminals of the switcher 155 using the touch panel 113.

Since the monitor A111a connected to the output terminal OUT1 and the monitor B111b connected to the output terminal OUT2 are capable of outputting the 2D video, 2D is set as the monitor type. Similarly, 3D is set as the monitor type for the output terminals OUT3 and OUT4, and 4K is set as the monitor type for the output terminals OUT5 and OUT6. The information set using the touch panel 113 in this way is inputted to the video output determination portion 172 through the touch panel control portion 171 and then stored in the data holding portion 174.

In addition, the video output determination portion 172 generates a setting table of the switcher in which the monitor type and the output destination of the monitor identification video are linked with each other from the information set in this way, and stores the setting table in the data holding portion 174.

FIG. 10 is a diagram for describing one example of a setting table 174b. As illustrated in FIG. 10, in the setting table 174b, in the case that the monitor type is 2D, from the information in FIG. 9, the output terminals OUT1 and OUT2 of the switcher 155 are associated as the output destinations of the monitor identification video. Similarly, in the setting table 174b, the output terminals OUT3 and OUT4 of the switcher 155 are associated as the output destinations of the monitor identification video from the information in FIG. 9 in the case that the monitor type is 3D, and the output terminals OUT5 and OUT6 of the switcher 155 are associated as the output destinations of the monitor identification video from the information in FIG. 9 in the case that the monitor type is 4K.

In addition, in the data holding portion 174, the monitor type and the monitor identification video are held in correspondence and the information on the peripheral device operation screen to be displayed on the touch panel 113 is also held.

Figure 11:
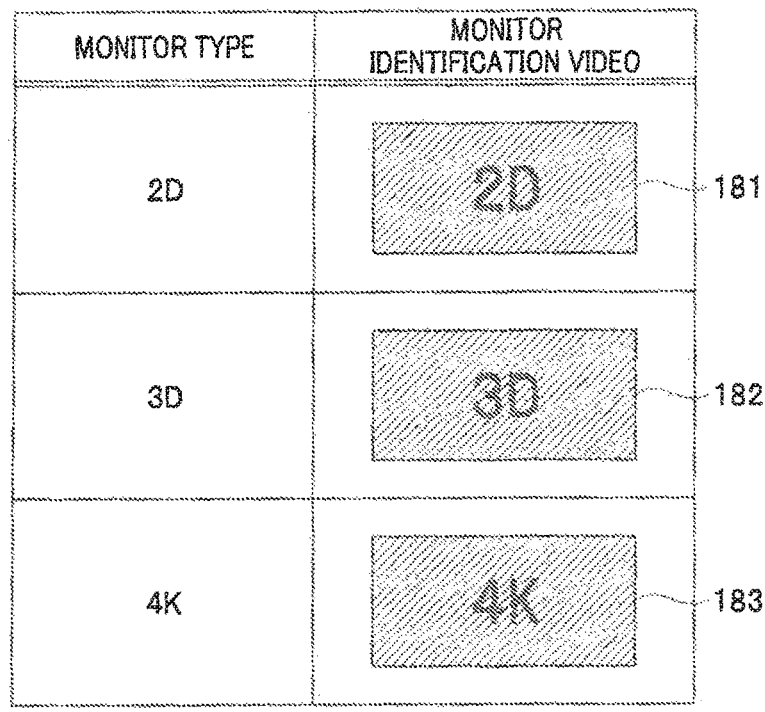
FIG. 11 is a diagram for describing one example of the monitor type and the monitor identification video corresponding to the monitor type.
Figure 12:
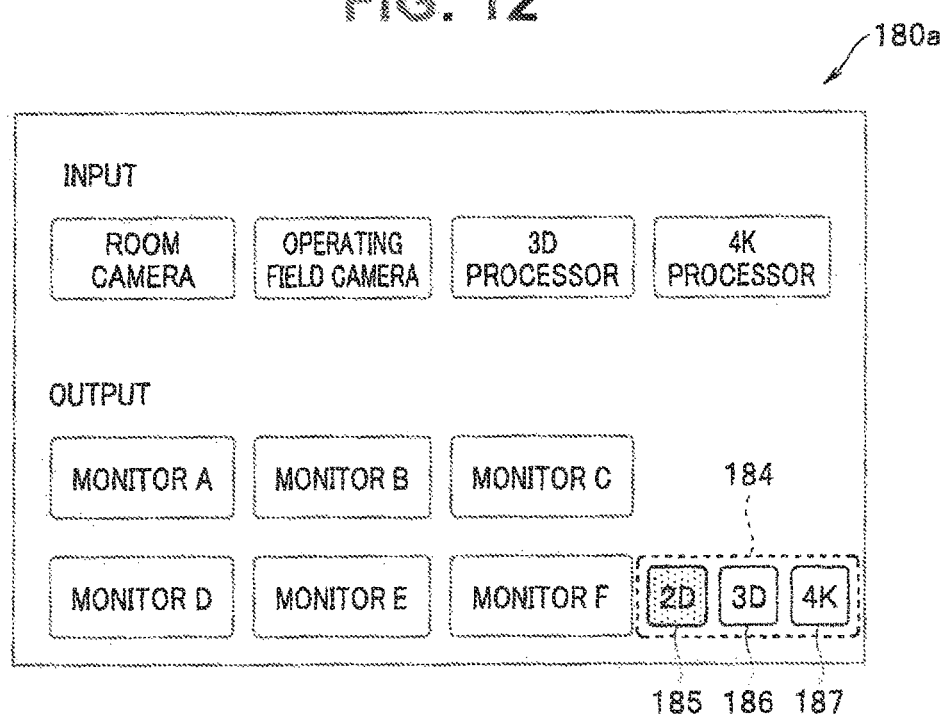
FIG. 12 is a diagram for describing one example of the peripheral device operation screen.

FIG. 11 is a diagram for describing one example of the monitor type and the monitor identification video corresponding to the monitor type, and FIG. 12 is a diagram for describing one example of the peripheral device operation screen.

As illustrated in FIG. 11, a monitor identification video 181 indicating 2D by outline characters is associated with the monitor type 2D. Similarly, a monitor identification video 182 indicating 3D by outline characters is associated with the monitor type 3D, and a monitor identification video 183 indicating 4K by outline characters is associated with the monitor type 4K.

In addition, as illustrated in FIG. 12, in the data holding portion 174, the information on a peripheral device operation screen 180a for operating the peripheral device is held. The peripheral device operation screen 180a is configured by adding monitor type identification buttons 184 to the peripheral device operation screen 180 in FIG. 6. The monitor type identification buttons 184 include a button 185 corresponding to the monitor type 2D, a button 186 corresponding to the monitor type 3D, and a button 187 corresponding to the monitor type 4K.

The information on the peripheral device operation screen 180a is read from the data holding portion 174 by the video output determination portion 172, and outputted to the touch panel control portion 171. The touch panel control portion 171 performs control of outputting the video of the peripheral device operation screen 180a to the touch panel 113. Thus, the peripheral device operation screen 180a is displayed on the touch panel 113.

When the user depresses the button 185 corresponding to the monitor type 2D, the touch panel depression signal is inputted through the touch panel control portion 171 to the video output determination portion 172. The video output determination portion 172 discriminates that the monitor type 2D is depressed from the touch panel depression signal, and outputs the video selection signal indicating the monitor type 2D to the data holding portion 174. In the data holding portion 174, according to the video selection signal, the monitor identification video 181 corresponding to the monitor type 2D is outputted to the video output portion 175. The video output portion 175 outputs the monitor identification video 181 from the data holding portion 174 to the switcher 155.

In addition, when it is recognized that the monitor type 2D is depressed on the peripheral device operation screen 180a, the video output determination portion 172 refers to the setting table 174b, acquires the switcher setting information, and outputs the switcher setting information to the peripheral device control portion 173. The peripheral device control portion 173 outputs the switcher control signal to the switcher 155, based on the switcher setting information from the video output determination portion 172. The switcher 155 outputs the monitor identification video 181 from the video output portion 175 to the monitor A111a and the monitor B111b according to the switcher control signal from the peripheral device control portion 173.

Figure 13:
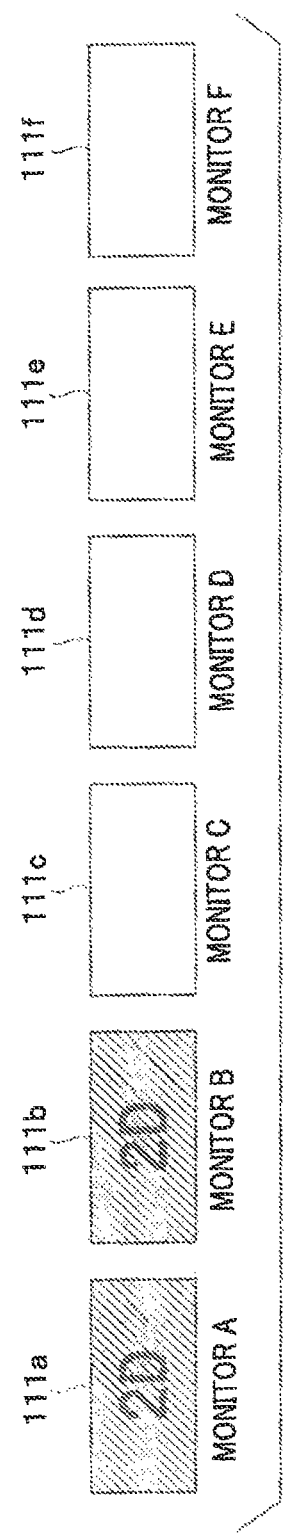
FIG. 13 is a diagram for describing one example of the video outputted to the monitor.

FIG. 13 is a diagram for describing one example of the video outputted to the monitor. As described above, in the case that the button 185 corresponding to the monitor type 2D is depressed on the peripheral device operation screen 180a, as illustrated in FIG. 13, the monitor identification video 181 in FIG. 11 is displayed on the monitor A111a and the monitor B111b. Note that, in the case that the button 186 corresponding to the monitor type 3D is depressed, by the similar processing, the monitor identification video 182 corresponding to the monitor type 3D is displayed on the monitor C111c and the monitor D111d. In addition, in the case that the button 187 corresponding to the monitor type 4K is depressed, by the similar processing, the monitor identification video 183 corresponding to the monitor type 4K is displayed on the monitor E111e and the monitor F111f.

By the above processing, the medical system 100 can display the type of the displayable video on the monitors A111a-F111f. As a result, the user can easily identify the monitors A111a-F111f capable of displaying the video signal of 2D, 3D and 4K.

Modification of Second Embodiment

Next, the modification of the second embodiment will be described.

Figure 14:
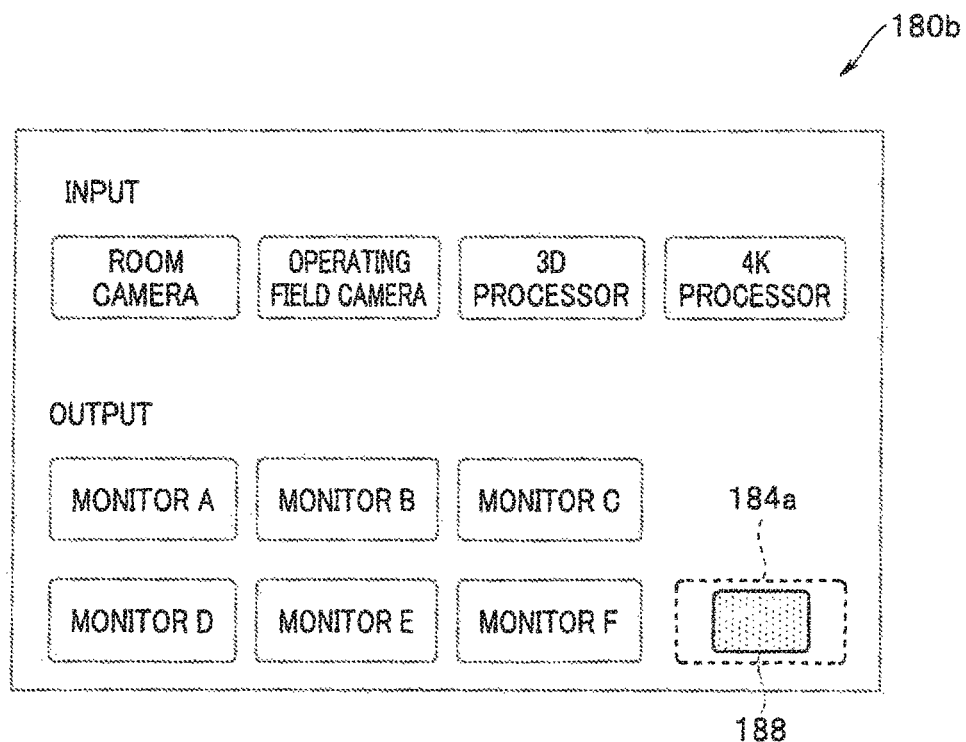
FIG. 14 is a diagram for describing one example of the peripheral device operation screen.

FIG. 14 is a diagram for describing one example of the peripheral device operation screen. As illustrated in FIG. 14, a peripheral device operation screen 180b is configured using a monitor type identification button 184a instead of the monitor type identification buttons 184 in FIG. 12. The monitor type identification button 184a includes a switching button 188. The peripheral device operation screen 180b is displayed on the touch panel 113 similarly to the embodiments described above.

When the monitor type identification button 184a displayed on the touch panel 113 is depressed, the video output determination portion 172 controls the data holding portion 174 to output the monitor identification videos 181-183 to the video output portion 175 at a predetermined interval (for example, at an interval of two seconds). The video output portion 175 outputs the monitor identification videos 181-183 to the switcher 155 at the predetermined interval.

In addition, when the monitor type identification button 184a displayed on the touch panel 113 is depressed, the video output determination portion 172 outputs the switcher setting information for switching output setting of the switcher 155 at the predetermined interval to the peripheral device control portion 173. The peripheral device control portion 173 outputs the switcher control signal to the switcher 155 and switches the output destination at the predetermined interval, based on the switcher setting information.

The switcher 155 outputs the monitor identification videos 181-183 inputted from the video output portion 175 at the predetermined interval to the monitors A111a-F111f for which the output destination is switched at the predetermined interval, based on the switcher control signal.

FIG. 15 is a diagram for describing one example of the video outputted to the monitor. As described above, in the case that the switching button 188 is depressed on the peripheral device operation screen 180b, as illustrated in FIG. 15, the monitor identification video 181 is displayed on the monitor A111a and the monitor BI 111b. After the predetermined interval, the output destination of the switcher 155 and the inputted monitor identification video are switched, and the monitor identification video 182 is displayed on the monitor C111c and the monitor D111d. Further, after the predetermined interval, the output destination of the switcher 155 and the inputted monitor identification video are switched, and the monitor identification video 183 is displayed on the monitor E111e and the monitor F111f.

In this way, when the switching button 188 is depressed, the output destination of the switcher 155 and the monitor identification videos 181-183 are switched at the predetermined interval. Thus, the monitor identification videos 181-183 can be outputted to the displayable monitors A111a-F111f at the predetermined interval in an order of 2D, 3D and 4K.

Note that the order of the monitor identification videos 181-183 outputted to the monitors A111a-F111f is not limited to the order of 2D, 3D and 4K, and may be other orders.

In addition, after the monitor identification video 183 is displayed on the monitors E111e and F111f, the monitor identification video 181 may be outputted to the monitors A111a-F111f, getting back to a beginning.

By the above processing, the medical system 100 can display the type of the displayable video on the monitors A111a-F111f at the predetermined interval. As a result, the user can easily identify the monitors A111a-F111f capable of displaying the video signal of 2D, 3D and 4K, similarly to the second embodiment.

Third Embodiment

Next, the third embodiment will be described.

FIG. 16 is a diagram describing one example of the detailed circuit configuration of the system controller 114. Note that, in FIG. 16, for components similar to the components in FIG. 3, same signs are attached and description is omitted.

As illustrated in FIG. 16, to the switcher 155, instead of the 3D-supporting monitor D111d in FIG. 3, a 2D/3D-supporting monitor G111g capable of displaying the two-dimensional image and the three-dimensional image is connected. In addition, the system controller 114 is configured using a peripheral device control portion 173a instead of the peripheral device control portion 173 in FIG. 3.

Generally, 2D/3D-supporting monitors include monitors that automatically switch display according to a kind (2D/3D) of video signal and monitors that cannot automatically switch display according to a kind of video signal. The 2D/3D-supporting monitor G111g of the present embodiment is described as the monitor that cannot automatically switch the display according to the kind of the video signal.

The peripheral device control portion 173a outputs a switching signal for switching a display mode between 2D and 3D to the monitor G111g. More specifically, the peripheral device control portion 173a controls the setting of the switcher 155, and switches the display mode from 3D to 2D when outputting the video (monitor identification videos 176-179 or 181-183) from the video output portion 175 to the monitor G111g. Then, when output of the monitor identification videos 176-179 or 181-183 to the monitor G111g is ended, the peripheral device control portion 173a switches the display mode from 2D to 3D.

Since the monitor identification videos 176-179 and 181-183 held in the data holding portion 174 are generally a 2D video signal, in the case of displaying the monitor identification video on the 3D-supporting monitor, the monitor identification video is not normally displayed. Therefore, in the case of the 2D/3D-supporting monitor G111g, the display mode is switched to 2D when the monitor identification videos 176-179 or 181-183 are displayed. As a result, the monitor identification videos 176-179 or 181-183 can be normally displayed on the monitor G111g.

As described above, according to the medical system of the present embodiment, the monitor identification videos 176-179 or 181-183 can be normally displayed on the monitor.

Note that, for the respective steps in the flowchart in the present description, unless contrary to the nature, an execution order may be changed, the plurality of steps may be simultaneously executed, or the steps may be executed in a different order for each execution.

The present invention is not limited to the embodiments described above, and various changes and modifications or the like are possible without changing a subject matter of the present invention.

What is claimed is:

1. A medical system comprising:
a plurality of monitors each configured to display a video signal of a different type;
a touch panel configured to display an operation screen where a selecting operation of an output destination of a video signal of a peripheral device is performed;
a video signal discrimination portion configured to discriminate, among the plurality of monitors, a monitor capable of displaying the video signal of the peripheral device selected by the touch panel by referring to a table in which the peripheral device is associated with the monitor capable of displaying the video signal;
a monitor information holding portion configured to hold a monitor identification video for identifying the monitor capable of displaying the video signal and information on the corresponding monitor; and
a control portion configured to perform control so as to display the monitor identification video held in the monitor information holding portion on the discriminated monitor, depending on a discrimination result of the video signal discrimination portion.

2. The medical system according to claim 1,
wherein the touch panel includes a monitor identification confirmation button configured to confirm a type of the monitor, and
the control portion displays the monitor identification video on the discriminated monitor when the monitor identification confirmation button is depressed.

3. The medical system according to claim 2, wherein the control portion displays the monitor identification video on the discriminated monitor in order at a predetermined interval when the monitor identification confirmation button is depressed.

4. The medical system according to claim 1, wherein, in a case that the monitor can switch a plurality of display modes, the control portion outputs a control signal for switching the display modes to the monitor when displaying the monitor identification video.

* * * * *